United States Patent [19]

Haber et al.

[11] Patent Number: 5,405,326

[45] Date of Patent: Apr. 11, 1995

[54] DISPOSABLE SAFETY SYRINGE WITH RETRACTABLE SHUTTLE FOR LUER LOCK NEEDLE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 112,447

[22] Filed: Aug. 26, 1993

[51] Int. Cl.⁶ .............................................. A61M 5/00
[52] U.S. Cl. .................................. 604/110; 604/195; 604/232
[58] Field of Search ............... 604/110, 187, 192, 195, 604/198, 232, 263

[56] References Cited

U.S. PATENT DOCUMENTS

| | | |
|---|---|---|
| 4,808,169 | 2/1989 | Haber et al. . |
| 4,826,489 | 5/1989 | Haber et al. . |
| 4,834,717 | 5/1989 | Haber et al. . |
| 4,892,107 | 1/1990 | Haber . |
| 4,909,794 | 3/1990 | Haber et al. . |
| 4,919,657 | 4/1990 | Haber et al. . |
| 4,931,040 | 6/1990 | Haber et al. . |
| 4,935,014 | 6/1990 | Haber . |
| 5,112,307 | 5/1992 | Haber et al. . |
| 5,116,319 | 5/1992 | Van Den Haak ................ 604/110 |
| 5,195,985 | 3/1993 | Hall .................................. 604/195 |
| 5,330,440 | 7/1994 | Stanners et al. .................. 604/195 |

Primary Examiner—John D. Yasko
Attorney, Agent, or Firm—Townsend & Townsend Khourie & Crew

[57] ABSTRACT

A disposable safety syringe has a needle shuttle slidably located within a main syringe barrel. The shuttle has a pair of outwardly extending guide tabs which engage a guide slot formed in the barrel wall. The upper end of the needle shuttle is configured to accept a luer lock needle assembly and has a downwardly extending spike used to penetrate the septum of an ampoule mounted in the barrel. A sleeve and rod assembly are mounted in the barrel below the ampoule and can be used to translate the ampoule from a suspended shipping position to an injecting position in which the septum is penetrated by the spike. The sleeve and rod assembly is removed after use, the spent ampoule is withdrawn and the needle shuttle is maneuvered downwardly by means of the guide tabs to a locking position in which the needle assembly is housed within the barrel for safe disposal.

13 Claims, 5 Drawing Sheets

DISPOSABLE SAFETY SYRINGE WITH RETRACTABLE SHUTTLE FOR LUER LOCK NEEDLE

BACKGROUND OF THE INVENTION

This invention relates to a relatively low cost, disposable syringe designed to reduce or eliminate accidental needle strikes by enabling selective position control of the needle from an injecting position to a retracted and locked position.

Hypodermic syringes are used for a variety of injection procedures including the delivery of medicinal drug and anesthetics to a patient. Once the injection procedure is completed, problems can arise if the syringe is not disposed of properly and adequately. Healthcare workers are susceptible to accidental and potentially infectious needle strikes if the needle is carelessly handled or broken during disposal of the syringe after use. If an accidental needle strike does occur, a blood test is typically required to determine whether the worker has been infected. The cost of performing such tests and the loss of personnel time attendant upon such tests can be particularly damaging to a healthcare facility striving for economy and efficiency.

There are several known syringes designed to provide retraction of a syringe needle after use. In some such designs, the apparatus is designed such that the needle is retracted within the same ampoule which initially housed the medication dispensed with the syringe. In other known devices, the retraction mechanism is designed to retract the used needle within the syringe housing and lock the needle in the retracted position.

While such known designs have been found suitable in a wide variety of applications, none is compatible with a standard syringe needle using the luer-lock design. In the luer lock design, a single ended needle is bonded to a plastic carrier member, the needle being received within a central opening formed in the carrier and bonded to the carrier by suitable adhesive. The carrier is provided with externally formed threads designed to threadably engage the syringe housing. Such needles have found wide use, and are available in several standard sizes. Consequently, the need exists for an economical disposable syringe which is compatible with the luer-lock type of needle assembly and which provides safe handling and disposal for such needle assemblies, as well as other attachable needle assemblies, after use.

SUMMARY OF THE INVENTION

The invention comprises a disposable safety syringe which is designed for use with the luer lock standard needle assembly, is relatively simple in design and use, and provides retractable locking for the needle after use, with the needle being positioned safely within the syringe barrel.

In the preferred embodiment, the invention includes a main housing having a wall portion with an interior volume, the wall portion having a guide slot with a tab support portion and a tab lock portion. The main housing interior volume preferably includes a limit stop region for limiting movement of a needle shuttle within the interior volume.

A needle shuttle dimensioned to be insertable within the interior volume of the main housing has a needle attachment portion, a penetrating member with a passageway, a pair of spaced detent members, and a guide tab locatable in the main housing guide slot. The needle attachment portion is designed to secure an attachable needle assembly, preferably a luer lock type needle assembly, and includes an internally threaded end portion preferably formed with luer lock threads. The closure penetrating member is designed to pierce a penetrable closure on the dispensing end of an ampoule when the ampoule is positioned within the main housing interior volume, the closure penetration member preferably comprising a spike portion extending longitudinally of the needle shuttle and located centrally thereof. The closure penetrating member is formed with a longitudinally extending fluid passageway, which preferably extends centrally of the spike portion, and the spike portion is preferably provided with an elongated crossbore in communicating with the passageway to facilitate the transfer of liquid therealong. The spaced detent members are engageable with the neck rim of an ampoule inserted in the main housing interior volume and provide detent support for the ampoule and two positions longitudinally of the main housing.

The needle shuttle guide tab enables manipulation of the needle shuttle between an injection position in which the guide tab is located in the tab support portion of the guide slot and a lock position in which the guide tab is located in the tab lock portion of the guide slot. In the locked position, the needle shuttle maintains an attached needle assembly within the interior volume of the main housing so that the needle is locked in a totally retracted position.

The needle shuttle preferably includes a pair of longitudinally extending wall members, and a pair of laterally spaced guide tabs formed on one of the pair of wall members. To facilitate insertion of the needle shuttle within the interior of the main housing, the wall member on which the guide tabs is located in inwardly flexible.

A sleeve and rod assembly is dimensioned to be inserted within the interior volume of the main housing for engaging the opposite end of an ampoule located in the interior volume and for shifting the ampoule within the interior volume from a first detent position to a second detent position. The sleeve and rod assembly further includes means engageable with a slidable piston located within the ampoule for translating the piston towards the dispensing end of the ampoule to expel the contents thereof via the needle shuttle passageway. The sleeve and rod assembly preferably includes a sleeve member having a first longitudinally extending bore, a counterbore with a larger diameter than the first bore, and a threaded portion located intermediate the first bore and the counterbore. The sleeve and rod assembly further preferably includes a rod member having a threaded portion engageable with the threaded portion of the sleeve member so that the sleeve member and the rod member may be moved in unison or separately. The sleeve member is preferably provided with a longitudinally extending cut-away for enabling the rod member to be press fitted into the first bore and the counterbore.

The invention is preferably configured for shipment in two subassemblies: a first subassembly including the main housing and the needle shuttle, and a second subassembly comprising the sleeve and rod. An ampoule may be included in the first subassembly, or may be supplied by the user. When the ampoule is supplied with the first subassembly, the ampoule is inserted within the interior of the main housing and maneuvered to the first detent position in which the penetrable closure member is located below the tip of the needle shuttle closure penetrating member. Similarly, the needle assembly may be supplied by the user or shipped along with the two subassemblies. When shipped with the two subassemblies, the needle assembly is preferably detached from the needle shuttle.

In use, the ampoule is inserted in the main housing-/needle shuttle sub-assembly to the first detent position by the user (unless already supplied), and the needle assembly is attached to the needle shuttle. Thereafter, the sleeve and rod assembly is inserted into the interior of the main housing and used to shift the ampoule from the first detent position to the second detent position. During this movement, the ampoule closure is penetrated by the needle shuttle closure penetrating member. Thereafter, the rod is detached from the sleeve, and the rod is used to force the ampoule piston towards the dispensing end of the ampoule, thereby expelling the ampoule contents.

After the ampoule contents are expelled, the sleeve and rod are withdrawn and the ampoule is ejected from the main housing by manipulating the needle shuttle by means of the guide tab toward the locking position. The needle assembly, which is attached to the needle shuttle, is automatically withdrawn within the interior of the main housing and locked in place by means of the locking engagement between the needle shuttle guide tab and the tab lock portion of the main housing guide slot.

For a fuller understanding of the nature and advantages of the invention, reference should be had to the ensuing detailed description taken in conjunction with the accompanying drawings.

DESCRIPTION OF THE PREFERRED EMBODIMENT

Figure 1:
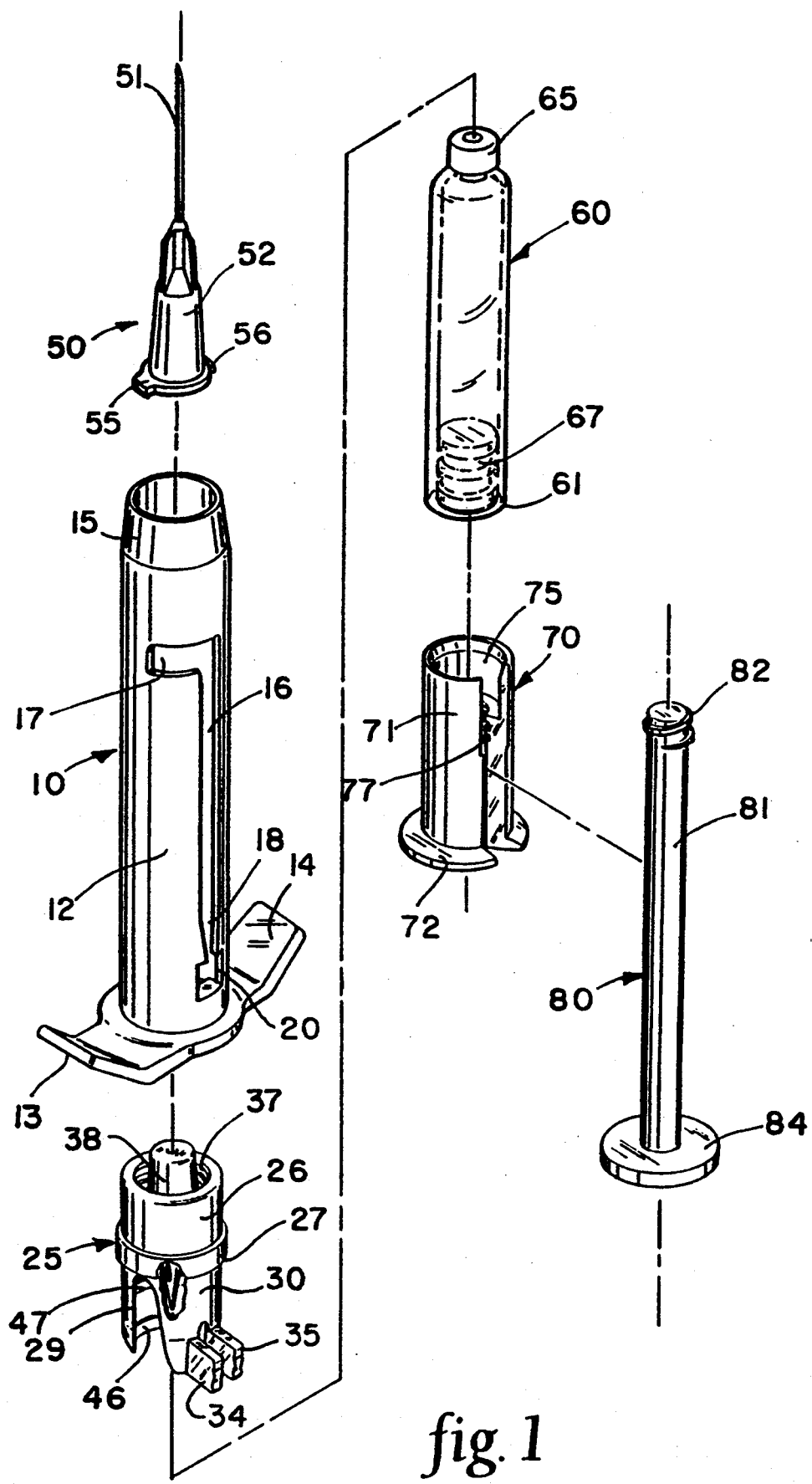
FIG. 1 is a perspective view of a preferred embodiment of the invention.
Figure 2:
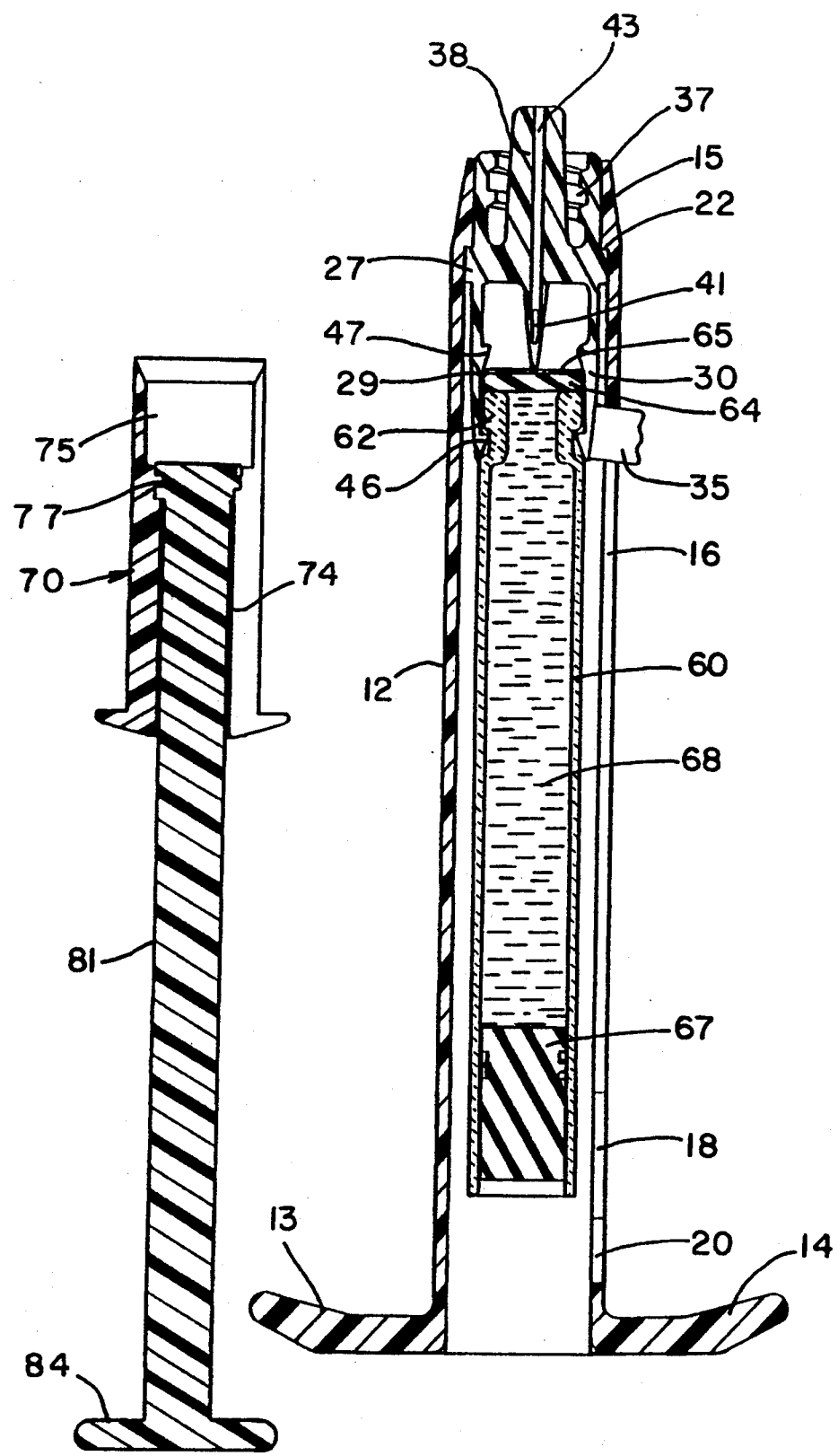
FIG. 2 is a sectional view illustrating the preferred embodiment of the invention prepared for packaging.
Figure 3:
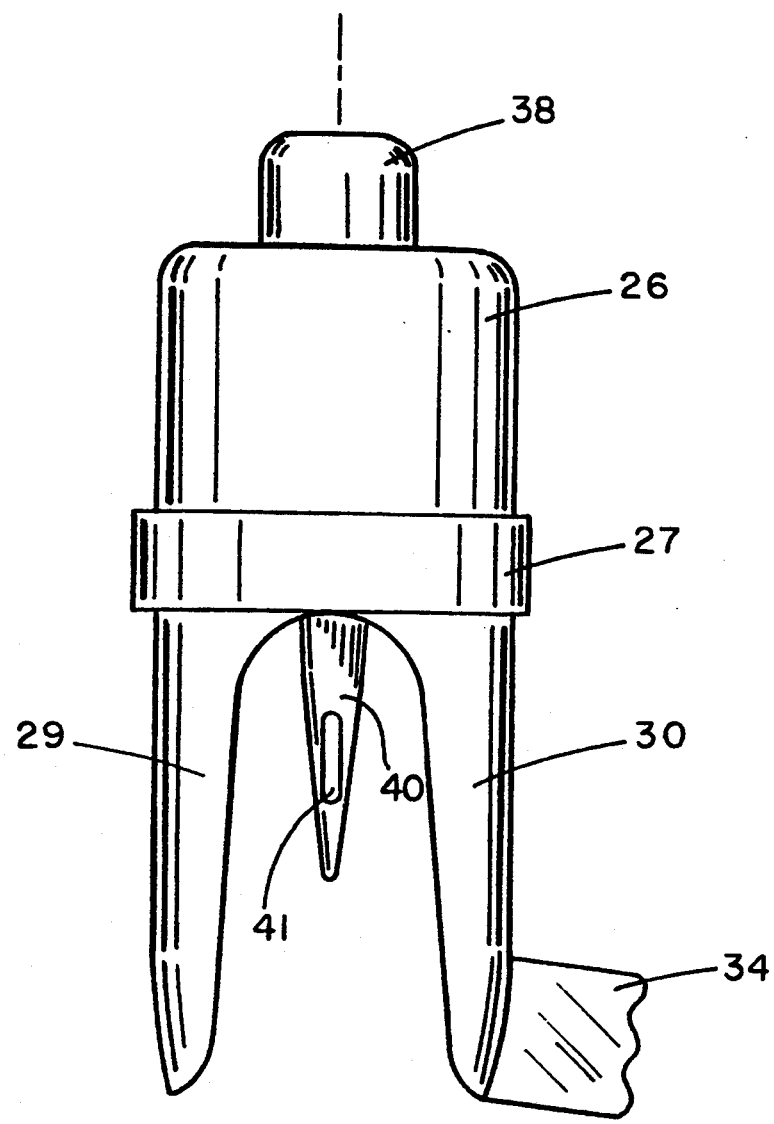
FIG. 3 is a side elevational view of the needle shuttle.

Turning now to the drawings, FIG. 1 is an exploded perspective view of the preferred embodiment of the invention. As seen in this Figure, the disposable syringe includes a main body member generally designated with reference numeral 10 having a barrel portion 12 with oppositely disposed upwardly extending angled finger tabs 13, 14 integrally formed at the bottom end thereof, and a beveled nose portion 15. Extending longitudinally of barrel portion 12 is a guide slot 16 terminating at the upper end in a laterally extending slot portion 17. Guide slot 16 also has a pair of mutually facing, inwardly tapering wall portions 18 terminating in an enlarged, generally rectangular lock slot portion 20. As best seen in FIG. 2, barrel 12 has an essentially cylindrical inner wall structure terminating at the upper end in a portion having a reduced diameter and forming an internal abutment edge 22.

Again with reference to FIG. 1, a one piece needle shuttle generally designated with reference numeral 25 has a generally cylindrical upper body section 26, an enlarged circumferentially extending waist portion 27 and a lower portion consisting of a pair of downwardly depending wall members 29, 30 each having a partially cylindrical configuration. Formed on wall member 30 is a pair of outwardly extending guide tabs 34, 35 which are laterally spaced by an amount which ensures a locking fit in lock slot 20 in the manner described more fully below.

As best seen in FIGS. 1 and 2, the upper body portion 26 of needle shuttle 25 has an internally threaded annular wall portion 37, and a centrally located tapered nose portion 38. Needle shuttle 25 also has a downwardly depending central spike portion 40 provided with a slightly elongated cross bore 41. A centrally located passageway 43 extends from the cross bore 41 to the top of the nose portion 38.

Lower wall portions 29, 30 are each provided with a pair of axially spaced detent ridges 46, 47 which are positioned and configured to engage the ampoule in the manner described below. It should be noted that threaded portion 37 of needle shuttle 25 is configured to accept a luer lock standard needle assembly shown in FIG. 1 and generally designated with reference numeral 50.

Needle assembly 50 includes a single ended needle 51 bonded within a unitary housing 52. Housing 52 has an internal passageway 54 (see FIG. 5) which is slightly tapered at the upper end to facilitate the insertion of needle 51, and the lower end of needle 51 is bonded within the lower portion of passageway 54 typically by means of a suitable adhesive. Needle housing 52 is provided with a pair of oppositely extending thread engaging tab portions 55, 56 designed to be rapidly engaged with threads 37 formed in the needle shuttle 25.

Again with reference to FIG. 1, a standard medicine cartridge or ampoule 60, typically fabricated from glass or pharmaceutically compatible plastic material, has an open lower end 61, and upper end with a central opening and an enlarged rim 62 (see FIG. 2). Ampoule 60 is sealed in a known manner using a septum 64 and a metal band 65 with a central opening formed therein. A sealing piston 67 is located in the bottom interior of ampoule 60 and seals the fluid contents 68 within ampoule 60 prior to dispensing.

An activation sleeve generally designated with reference numeral 70 has a generally cylindrical main body portion 71 terminating in an outwardly extending lower flange 72. Sleeve 70 is provided with a longitudinally extending bore 74 (see FIG. 2) communicating with an enlarged counter bore 75 dimensioned to accommodate the bottom end of ampoule 60. An intermediate threaded portion 77 is provided to enable a activation rod 80 to be removably attached to sleeve 70 in the manner described below. A portion of main body member 71 and flange 72 is cut away from sleeve 70 so that the stem portion 81 of the activation rod 80 can be pressed into the interior of sleeve 70.

In addition to stem portion 81, activation rod 80 has an upper threaded section 82 engageable with threaded section 77 of sleeve 70, and a lower enlarged base portion 84.

In use, the device is assembled in the following fashion. The nose portion 38 of needle shuttle 25 is inserted into the bore of barrel 12 from below and manipulated upwardly. The wall members 29, 30 are flexed together in order to permit locking tabs 34, 35 to clear the first portion of the inner wall of barrel 12. Shuttle 25 is manipulated further upwardly within barrel 12 until the locking tabs 34, 35 extend through the guide slot 16 in barrel 12. Thereafter, shuttle 25 can be manipulated upperwardly by means of the protruding guide tabs 34, 35 until the shuttle 25 is in the uppermost position at which the upper edges of the guide tabs 34, 35 encounter the upper edge of the slot portion 17. Thereafter, shuttle 25 is rotated by means of the guide tabs 34, 35 into the slot portion 17 so that the shuttle is supported by the lower edge of slot portion 17. If the syringe is to be shipped with the ampoule 60, ampoule 60 is now inserted via the bottom opening in barrel 12 and maneuvered upwardly therein until the lower edge of rim 62 passes the lower detent ridges 46 formed in shuttle 25. Ampoule 60 is now supported within barrel 12 in the attitude illustrated in FIG. 2 in which the tip of the spike 40 is positioned above band 65 and septum 64. The stem 81 of rod 80 is pressed fitted into shuttle 70 and may be threadably attached by rotating rod 80 in the proper direction. This shipping configuration for the invention is illustrated in FIG. 2. In some applications, the end user will supply the needle assembly 50: in such applications, the two subassemblies illustrated in FIG. 2 are shipped in the package to the user. In other applications, the needle assembly 50 is supplied along with the two subassemblies in the same package.

Figure 4:
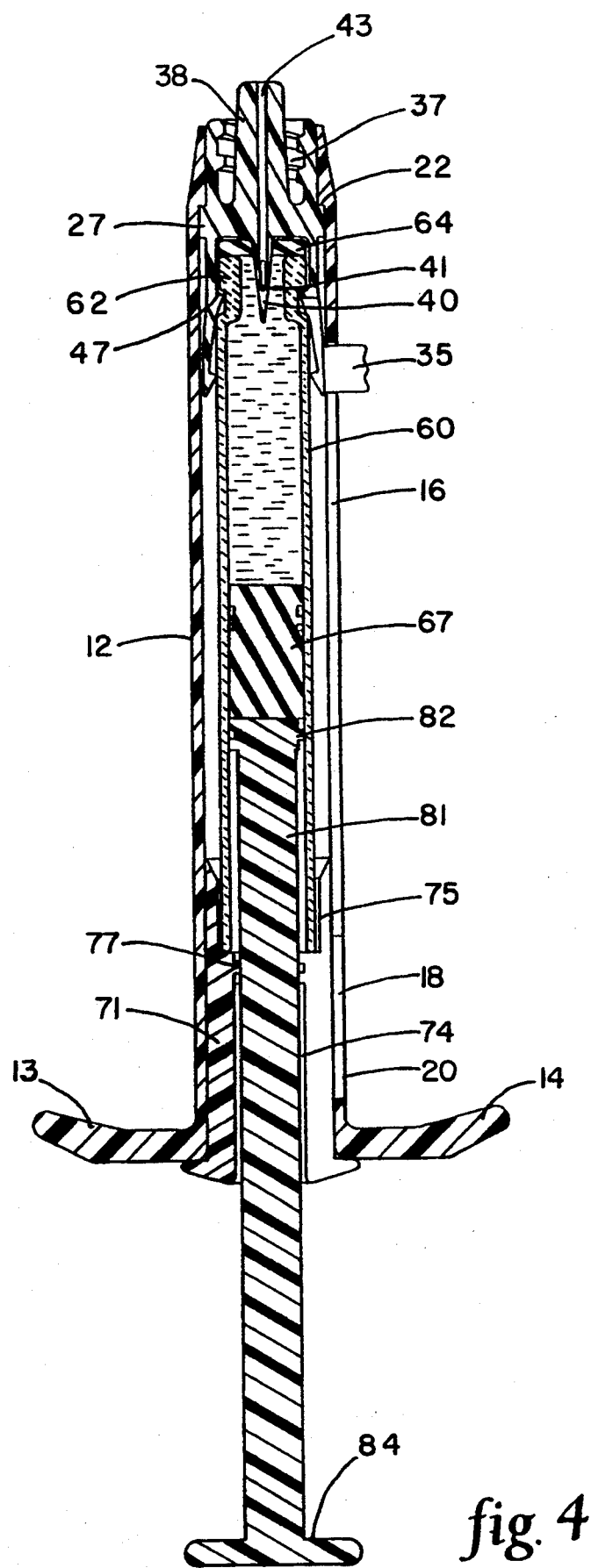
FIG. 4 is a sectional view of the invention after penetration of the ampoule septum.

When the syringe is scheduled to be used for an injection, the upper end of sleeve 70 is inserted into the lower end of barrel 16 and maneuvered upwardly until the lower end of ampoule 60 is snugly received in counter bore 75 of sleeve 70. Next, an upward force is applied by the user to sleeve 70 by means of rod 80, which causes sleeve 70 to force ampoule 60 upwardly to the second detent position illustrated in FIG. 4 in which the rim 62 of ampoule 60 is engaged by upper detent ridges 47. As seen in FIG. 4, in this position, spike 40 has pierced through the septum 64 and is located within the interior of ampoule 60 with the cross bore 41 immersed in the liquid within ampoule 60. Although not illustrated in FIG. 4 (due to space limitations), it is envisioned in normal use that the needle assembly 50 will be threaded onto the needle shuttle 25 prior to piercing of the septum 64.

Next, rod 80 is rotated in the appropriate direction to release rod 80 from sleeve 70 and permit free upper translation of rod 80 within barrel 12. This causes piston 67 within ampoule 60 to be translated upwardly and expel the contents of ampoule 60 via cross bore 41, passageway 43 and needle 51.

Figure 5:
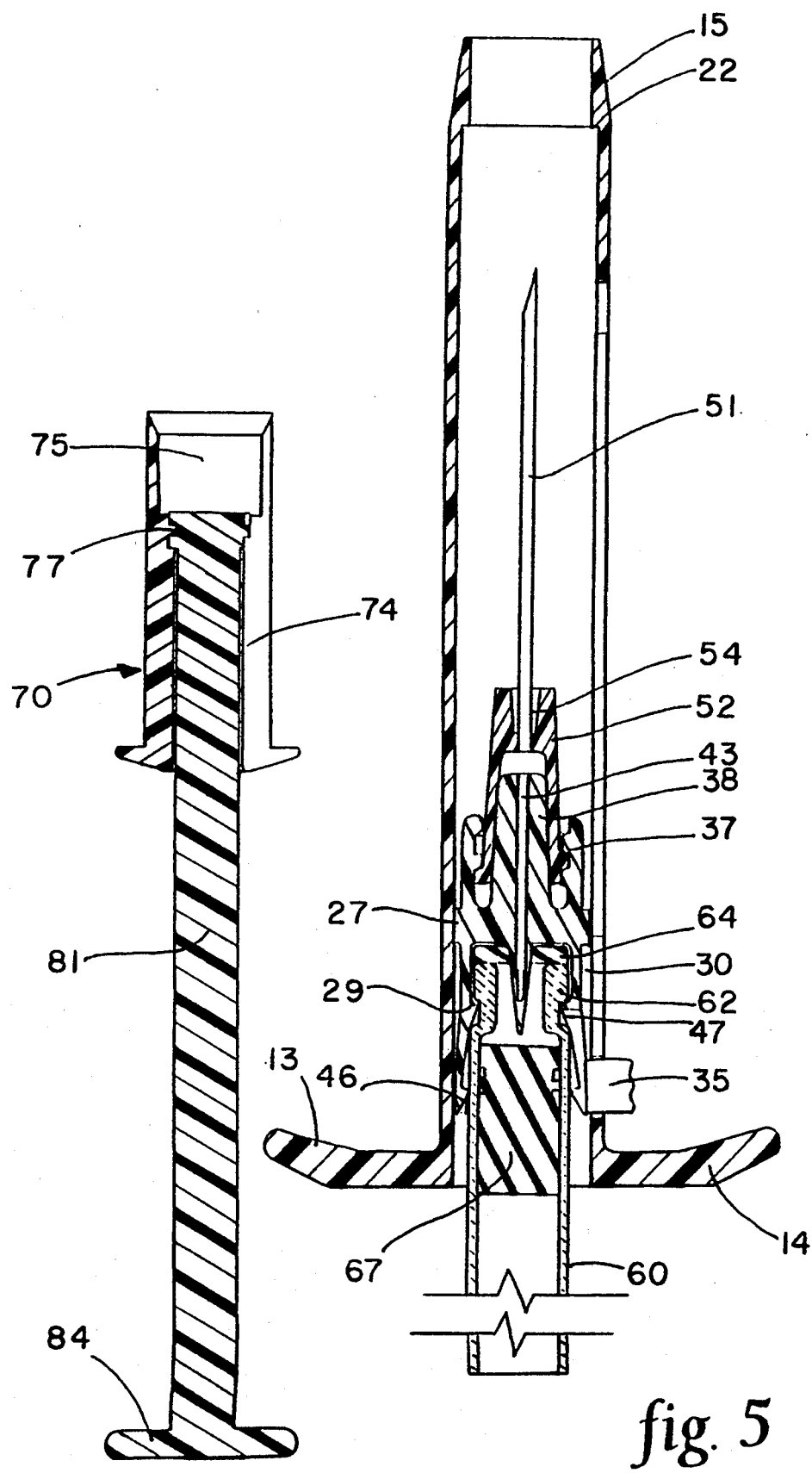
FIG. 5 is a sectional view of the invention in condition for disposal and illustrating the needle in the retracted locked position.

After the contents of ampoule 60 have been expelled by the required amount, rod 80 and sleeve 70 are manually withdrawn through the bottom opening in barrel 12. Thereafter, needle shuttle 25 is rotated by rotating guide tabs 34, 35 to the guide slot 16 and needle shuttle 25 is manipulated downwardly until the guide tabs 34, 35 are engaged in the lock slot 20. As the needle shuttle 25 is manipulated downwardly, the needle assembly is withdrawn into the interior of barrel 12 until the position illustrated in FIG. 5 is achieved. As seen in this Figure, the needle 51 is locked in place entirely within the barrel 12. Both subassemblies illustrated in FIG. 5 may now be disposed of.

As will now be apparent, disposable syringes fabricated according to the teachings of the invention are completely compatible with standard luer lock needle assemblies, and provide a safe and economical technique for disposing of used luer lock type needles. In addition, the invention affords additional protection by virtue of the fact that the needle need only be attached to the syringe just prior to puncturing the septum 64 in the ampoule 60. Further, during installation of ampoule 60 inadvertent pressure buildup within the ampoule 60 due to the accidental application of force to the bottom of piston 67 can be completely avoided by using the shuttle 70 and rod 80 to maneuver the ampoule 60 upwardly into the second detent position. In addition, due to the simplicity of the design of the invention, the ampoule 60 may be readily inserted at the user end in those applications in which it is not desired to transmit the ampoule 60 from the syringe supplier to the user.

While the above provides a full and complete disclosure of the preferred embodiment of the invention, various modifications, alternate constructions and equivalents may be employed as desired. For example, although expressly designed for use with luer lock type needle assemblies, the device can be adapted for use with any other type of standard or custom designed attachable needle assemblies in which the needle is housed in a base capable of interlocking engagement with a needle shuttle. Therefore, the above description should not be construed as limiting the scope of the invention, which is defined by the appended claims.

What is claimed is:

1. A disposable syringe for use with an attachable needle assembly and an ampoule having a main body portion, a dispensing end with a neck rim, a penetrable closure for the dispensing end and an opposite end with a piston for expelling the contents of the ampoule, said syringe comprising:

a main housing having a wall portion with an interior volume, said wall portion having a guide slot with a tab support portion and a tab lock portion;

a needle shuttle having a needle attachment portion, a closure penetrating member with a passageway, a pair of spaced detent members engageable with the neck rim of an ampoule when located in said interior volume of said main housing for providing first and second detent positions for the ampoule, and a guide tab engageable in said guide slot; and a sleeve and rod assembly insertable within said interior volume of said main housing for engaging the opposite end of an ampoule when located in said interior volume and for shifting the ampoule within said interior volume from said first detent position to said second detent position, said needle closure penetrating member of said needle shuttle being arranged to penetrate the ampoule closure when the ampoule is shifted between said first and second detent positions and the needle shuttle guide tab is located in the tab support portion of the housing guide slot, said sleeve and rod assembly further including means engageable with the ampoule piston for translating the piston towards the dispensing end of the ampoule to expel the contents via the needle shuttle passageway, said needle shuttle maintaining an attached needle assembly within said interior volume of said main body housing when the needle shuttle guide tab is located in the tab lock position of said guide slot.

2. The invention of claim 1 wherein said main housing interior volume includes a limit stop region for limiting movement of said needle shuttle therealong.

3. The invention of claim 1 wherein said needle attachment portion of said needle shuttle includes an internally threaded end portion.

4. The invention of claim 3 wherein said internally threaded end portion is formed with luer lock threads.

5. The invention of claim 1 wherein said needle shuttle closure penetrating member comprises a spike portion extending longitudinally of said needle shuttle and located centrally thereof.

6. The invention of claim 5 wherein said needle shuttle passageway extends centrally of said spike portion.

7. The invention of claim 6 wherein said needle shuttle further includes an elongated crossbore formed through said spike portion in communication with said passageway.

8. The invention of claim 1 wherein said needle shuttle includes a pair of laterally spaced tab portions.

9. The invention of claim 8 wherein said needle shuttle includes a pair of longitudinally extending wall members; and wherein said laterally spaced tab portions are formed on one of said wall members.

10. The invention of claim 9 wherein said one of said wall members is flexible.

11. The invention of claim 1 wherein said sleeve and rod assembly includes a sleeve member having a first longitudinally extending bore with a first diameter, a counterbore having a second diameter larger than said first diameter, and a threaded portion located intermediate said first bore and said counterbore.

12. The invention of claim 11 wherein said sleeve and rod assembly further includes a rod member having a threaded portion engageable with said threaded portion of said sleeve member.

13. The invention of claim 12 wherein said sleeve member is provided with a longitudinally extending cut-away for enabling said rod member to be press fitted into said first bore and said counterbore.

* * * * *